United States Patent [19]

Yerman

[11] Patent Number: 5,727,455
[45] Date of Patent: Mar. 17, 1998

[54] AUTOMATIC SYRINGE DESTRUCTION SYSTEM AND PROCESS

[76] Inventor: Arthur J. Yerman, 76 Grand Ave., Toms River, N.J. 08753

[21] Appl. No.: 631,655

[22] Filed: Apr. 1, 1996

[51] Int. Cl.⁶ .............................. B30B 15/34; B30B 1/32
[52] U.S. Cl. .................. 100/38; 100/73; 100/215; 100/223; 100/244; 100/318; 241/606
[58] Field of Search ..................... 100/38, 71, 73, 100/92, 215, 223, 244, 251, 264, 269.06, 316–318, 902, 101; 241/606

[56] References Cited

U.S. PATENT DOCUMENTS

| | | | |
|---|---|---|---|
| 2,763,202 | 9/1956 | Gramelspacher | 100/71 |
| 3,072,362 | 1/1963 | Allen . | |
| 3,188,018 | 6/1965 | Van Otteren . | |
| 3,383,228 | 5/1968 | Rekate et al. | 100/71 |
| 3,958,936 | 5/1976 | Knight, Jr. . | |
| 4,076,321 | 2/1978 | Haight et al. . | |
| 4,860,958 | 8/1989 | Yerman . | |
| 4,984,748 | 1/1991 | Kimura | 241/606 |
| 4,993,882 | 2/1991 | Nishizuka et al. . | |
| 4,995,765 | 2/1991 | Tokuhiro et al. . | |
| 5,003,892 | 4/1991 | Bricken . | |
| 5,215,412 | 6/1993 | Rogoff et al. . | |
| 5,365,982 | 11/1994 | O'Neill | 100/902 |
| 5,605,094 | 2/1997 | Besnier | 100/92 |

FOREIGN PATENT DOCUMENTS

| | | | |
|---|---|---|---|
| 58-132400 | 8/1983 | Japan | 100/902 |
| 59-16697 | 1/1984 | Japan | 100/902 |
| 8003576 | 8/1981 | Sweden . | |

*Primary Examiner*—Stephen F. Gerrity
*Attorney, Agent, or Firm*—McAulay Fisher Nissen Goldberg & Kiel, LLP

[57] ABSTRACT

An automatic syringe destruction system for sterilizing and destroying a carrier storing plastic syringes. A transfer wheel stores a plurality of carriers requiring sterilization and destruction. A first piston mechanism contacts one of the carriers stored on the transfer wheel and places the carrier into one end of a compression chamber. An induction coil surrounds the compression chamber and supplies heat to the compression chamber. A second piston mechanism enters another end of the compression chamber and compresses the carrier against the first piston mechanism.

11 Claims, 9 Drawing Sheets

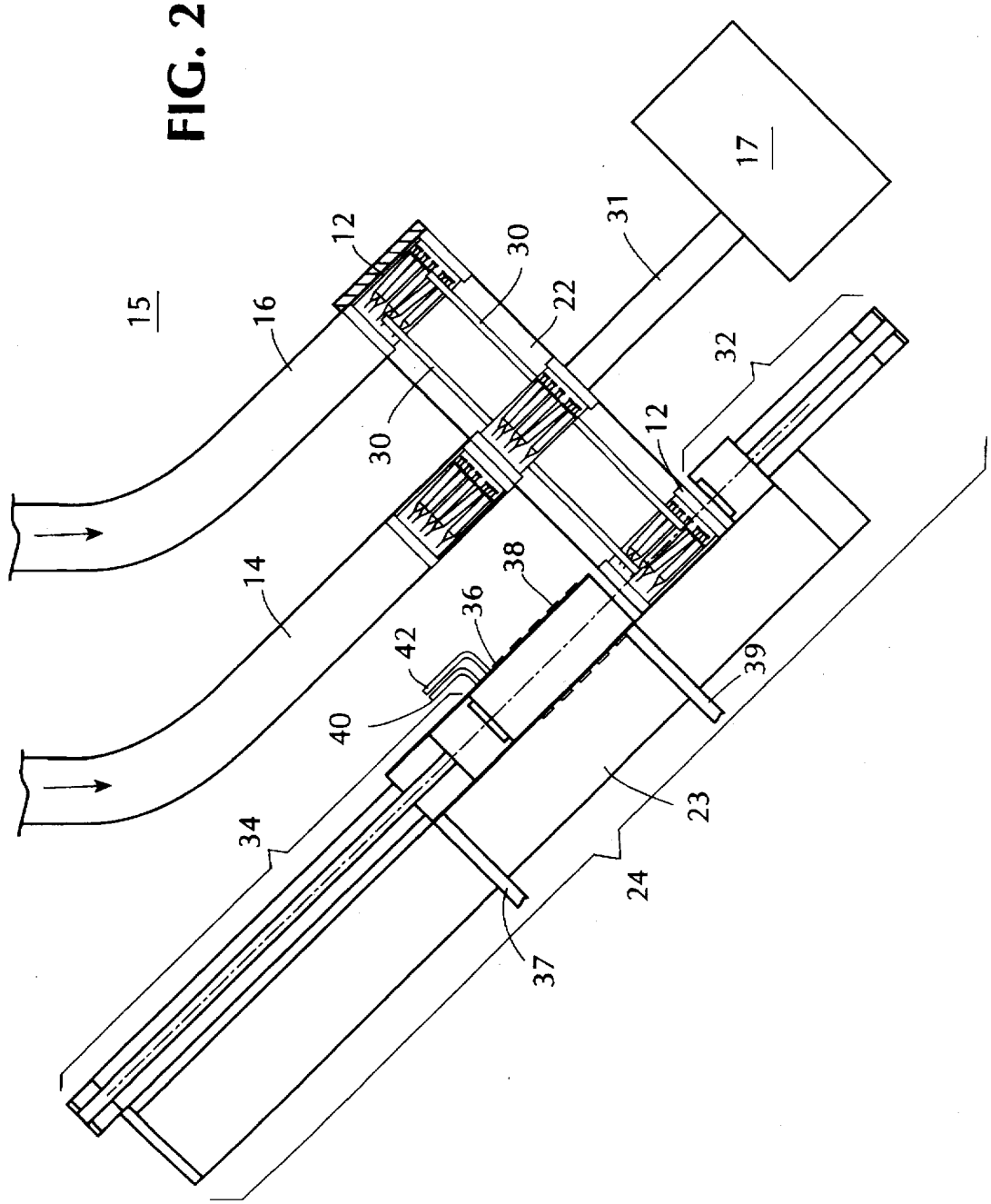

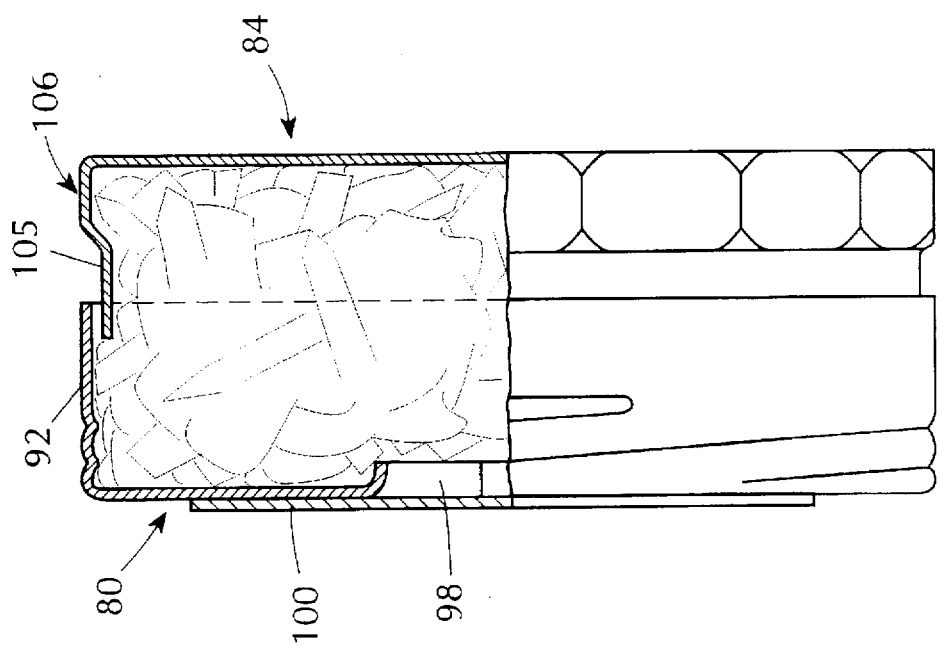
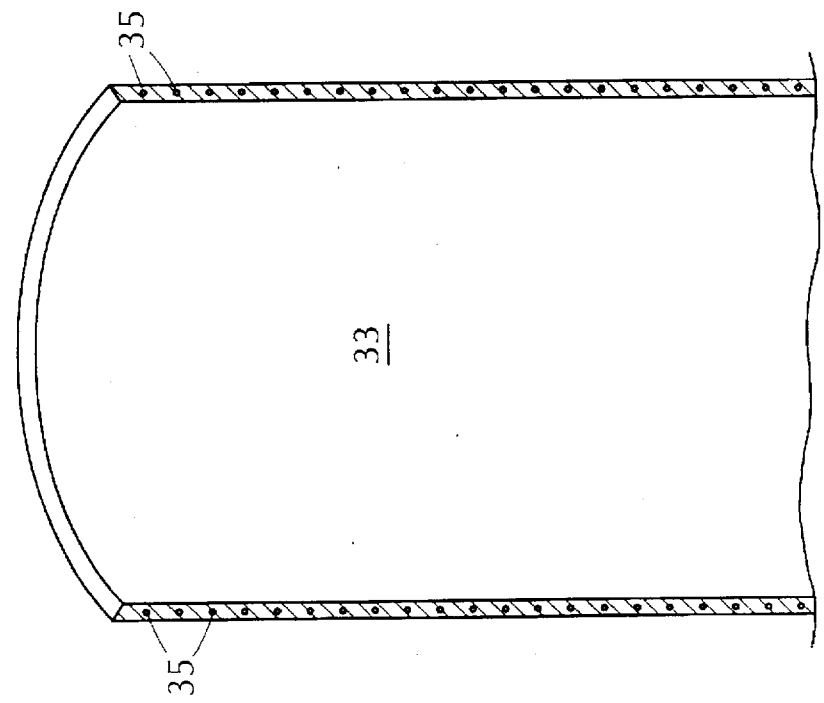

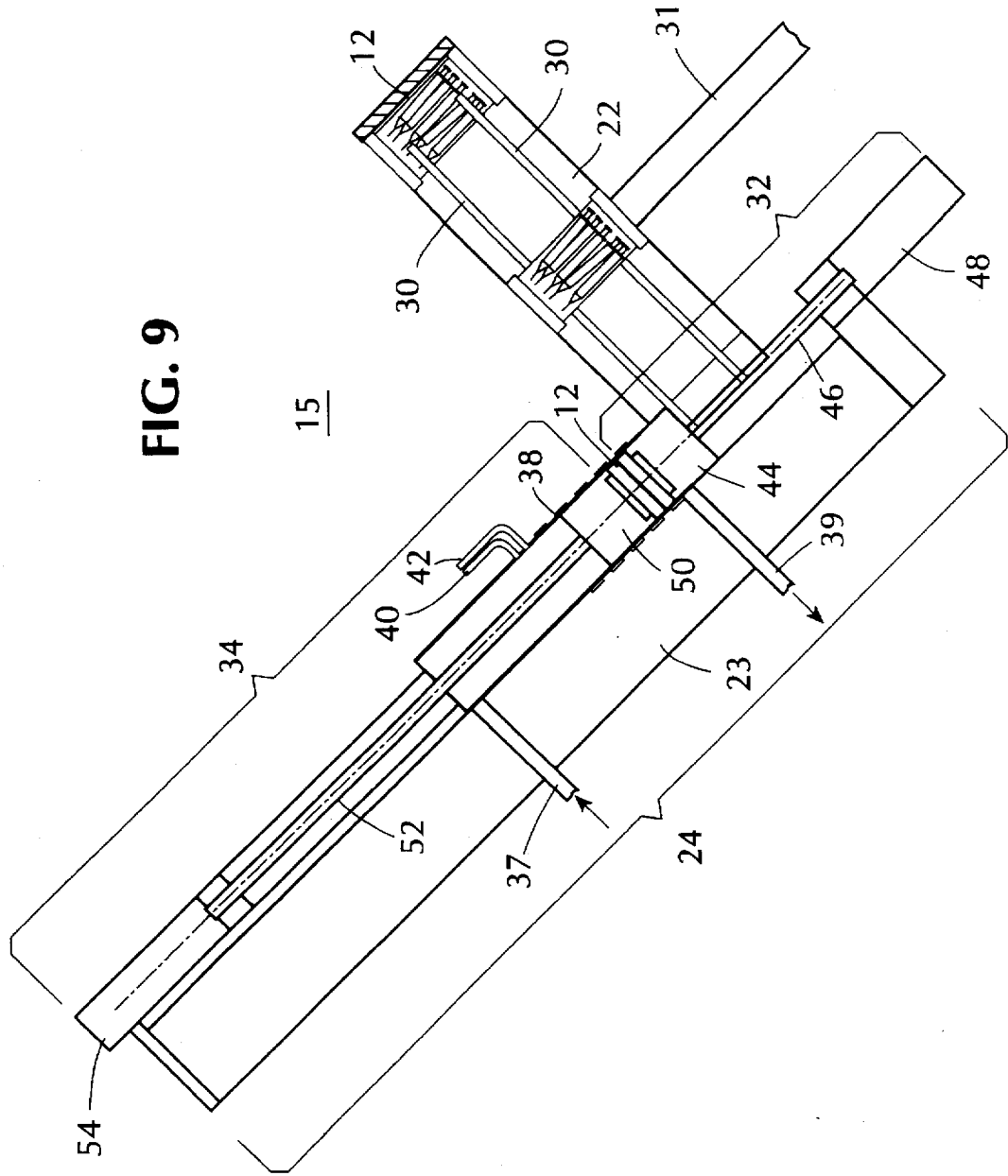

5,727,455

1

AUTOMATIC SYRINGE DESTRUCTION SYSTEM AND PROCESS

FIELD OF THE INVENTION

The present invention relates to a syringe destruction system and more particularly to a syringe destruction system which can automatically process a large number of containers holding syringes for sterilization and disposal.

BACKGROUND OF THE INVENTION

It is well known throughout the world that plastic syringes play a key role in the spread of infectious diseases. A number of factors are attributable to the undesirable spread of diseases caused by plastic syringes. Most notably are syringe sharing by addicts, inadvertent sticks of physicians and nurses attempting to recap a needle of a syringe, as well as inadvertent sticks of refuse handlers during the disposal process of the syringes.

Plastic syringes have also caused environmental problems. Syringes have been found to wash-up on beaches due to ocean dumping and appear on street surfaces due to flooding of storm drains or sewers.

In virtually all of these cases, these problems are caused by an inadequate means of destruction at the point of use of the syringe. To address this problem, conventional syringe destruction systems have been developed.

Conventional syringe destruction systems perform a variety of functions and are available in various sizes and designs. U.S. Pat. No. 5,003,892, for example, shows a syringe destruction system in which one or more plastic syringes are placed in a heat conductive container. The heat conductive container is sealed with and lid manually placed in an oven assembly. The oven assembly is heated at a predetermined temperature for a predetermined amount of time to melt the syringes. A sterile molten mass which is formed from the heating process is then cooled and removed for disposal.

U.S. Pat. No. 4,860,958 also shows a syringe destruction system. This system employs a cylinder with an open upper end into which a number of used plastic syringes are placed. A cover is placed over the open end of the cylinder, water is injected into the cylinder, and the cylinder is heated by heating elements to a temperature sufficient to melt the syringes. Once this occurs, a piston compacts the heated syringes to remold them into a sterilized compacted mass. The sterilized compacted mass is then cooled and removed for disposal.

Swedish patent application 8003576-9 shows another variation of conventional syringe destruction devices. In this apparatus, used plastic syringes with needles are placed in one or more plastic containers. The plastic containers including the used syringes are placed on a metal tray. The metal tray and containers are then placed in an oven and heated at a predetermined temperature for a sufficient amount time to melt both the containers and syringes. Once cooled, the tray with the melted containers and syringes is removed for disposal.

Conventional syringe destruction systems such as the ones described above are, however, limited in use. A primary drawback with conventional syringe destruction systems is that they are not capable of automatically processing containers holding syringes for sterilization and disposal. In particular, in the conventional syringe destruction systems, containers with used plastic syringes have to be manually retrieved and placed into a disposal system. As a result, sterilizing and disposing of used syringes with these systems can be cost prohibitive. Conventional syringe destruction systems have additional drawbacks as well. Namely, conventional syringe destruction systems are not capable of receiving a large number of containers with used syringes nor are they capable of receiving containers with used syringes from more than one location.

OBJECTS AND SUMMARY OF THE INVENTION

It is accordingly an object of the present invention to provide a syringe destruction system which can automatically process containers holding syringes for sterilization and disposal.

It is another object of the invention to provide an automatic syringe destruction system which can receive a large number of containers with used syringes from numerous locations.

It is yet another object of the invention to provide an automatic syringe destruction system which can benefit the public safety and health by producing a compacted mass which is sterile, safe to handle, recyclable, and environmentally sound.

In accordance with one aspect of the invention, an automated syringe destruction system is provided comprising: a carrier including plastic syringes requiting destruction and sterilization; a network for receiving a plurality of the carriers from multiple locations and transporting the carriers to a centralized location; and a means for destroying and sterilizing the carriers received from the network at the centralized location.

The means for destroying and sterilizing the carriers further comprises: a transfer wheel for storing carriers received from the network; and, a destruction means for compacting the carriers contained on the transfer wheel.

The destruction means further includes: a rigid body for supporting the transfer wheel; a compression chamber which is attached to the rigid body above the transfer wheel, the compression chamber including first and second ends, a water port and a vacuum port; a first piston means for contacting one of the carriers stored on the transfer wheel and placing the carrier into the first end of the compression chamber, the first piston means being attached to the rigid body beneath the transfer wheel and in direct alignment with the compression chamber; an induction coil surrounding the compression chamber for supplying heat to the compression chamber; and a second piston means for entering the second end of the compression chamber to contact and compress the carrier against the first piston means, the second piston means being attached to the rigid body above the compression chamber and in direct alignment with the pressure chamber, wherein the water port supplies water to the compression chamber and the vacuum port applies a negative air pressure to the compression chamber.

The compression chamber includes a side wall which defines a hollow passage for processing water to cool the compression chamber.

The transfer wheel includes: a circular base defining a slot and a hole; a cylindrical-shaped body defining a slot which is attached to the circular base; a shaft which is rotatably inserted into the hole; and at least one circular guide with semicircular arcs recessed along its outer edge for securing the carriers, the circular guide being rotatably fit within the cylindrical-shaped body and integrally connected to the shaft.

The carrier comprises: a plastic tube including a first end and a second end; a first cover including a first metal surface defining an opening and a first metal tubular side wall which is connected to the first metal surface; a second cover including a second metal flat surface and a second metal tubular side wall which is connected to the second metal flat surface; wherein, the first metal cover is connected to the first end of the plastic tube and the second metal cover is connected to the second end of the plastic tube.

The carrier further includes: a pivot shaft which is attached to the first metal surface; and a swing cover which is is rotatably attached to the first metal surface by the pivot shaft to cover the opening. The carrier is constructed so that a diameter of the first metal tubular side wall is larger than a diameter of the second tubular side wall.

In accordance with another aspect of the invention, a method is provided for automatically destroying and sterilizing plastic syringes stored in a carrier. The method comprises the steps of (i) placing a plurality of carriers storing plastic syringes on a transfer wheel; (ii) transferring one of the plurality of carriers placed on the transfer wheel into a first end of a compression chamber with a first piston means; (iii) heating the compression chamber to a predetermined temperature; (iv) applying a vacuum pressure to the compression chamber; (v) injecting water into the compression chamber; (vi) removing water from the compression chamber; (vii) inserting a second piston means into a second end of the compression chamber to contact the carrier and compact the carrier against the first piston means; and, (viii) removing the compacted carrier from the compression chamber.

BRIEF DESCRIPTION OF THE DRAWINGS

The accompanying drawings are included to provide an understanding of the invention and constitute a part of the specification.

FIG. 2 illustrates a cross-sectional view of a syringe destruction apparatus in accordance with the present invention;

FIG. 5 illustrates a cross sectional view of a compression chamber used with a syringe destruction system in accordance with the present invention;

FIG. 8 illustrates a carrier used syringes after destruction and sterilization by a syringe destruction system in accordance with the present invention;

FIG. 9 illustrates the syringe destruction apparatus shown in FIG. 4, where the carrier had been compressed in accordance with the present invention; and, FIG. 10 illustrates the syringe destruction apparatus shown in FIG. 9 where the compressed carrier is positioned for removal in accordance with the present invention.

DETAILED DESCRIPTION OF THE INVENTION

Figure 1:
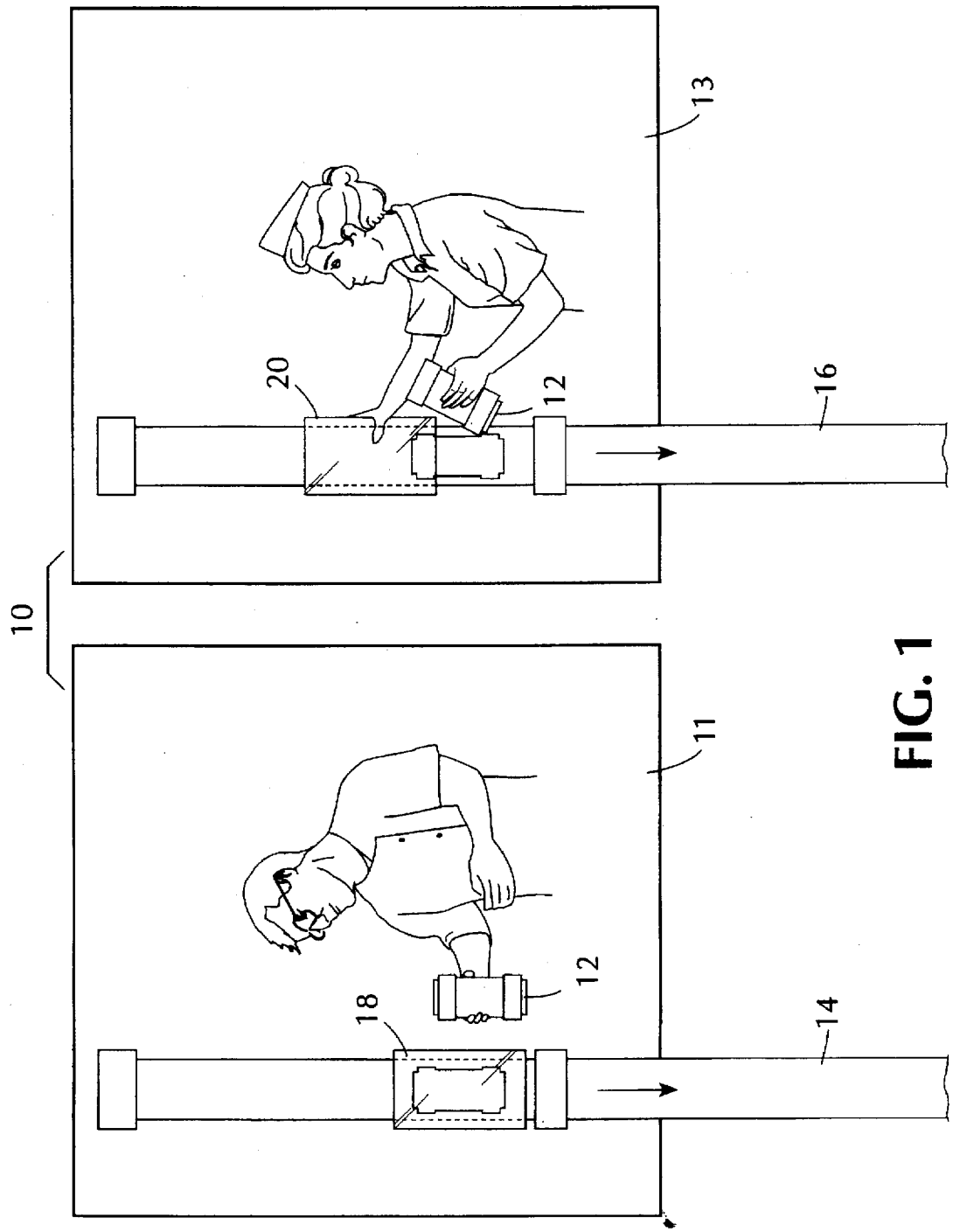
FIG. 1 illustrates a network for receiving carriers with used syringes from more than one location in accordance with the present invention.

FIG. 1 shows two remote stations 11 and 13 which are part of a network 10 for transporting carriers 12 in accordance with the present invention. Each carrier 12 is constructed so as to contain a plurality of used plastic syringes which require sterilization and destruction.

Remote stations, such as 11 and 13, can be installed in as many wards, stations, or rooms of a building as is necessary to allow for efficient depositing of plastic syringes after use. The network 10 typically comprises hollow pipes 14 and 16 which are installed within the building, such as a hospital, and which are interconnected to deliver the carriers 12 to a centralized location which is not shown. The pipes 14 and 16 respectively include receiving stations 18 and 20 for receiving the carriers 12. The stations 18 and 20 are located at different physical locations within the building to allow multiple users to access the network 10. The carriers 12 typically move through the network 10 by means of gravity. In an alternative embodiment, the network 10 can transport the carriers 12 by use of a negative air pressure generated by a vacuum pump or motor placed at the centralized location.

Referring to FIG. 2, the ends of the of pipes 14 and 16 are are connected to an apparatus 15 for destroying and sterilizing the carriers 12. The apparatus 15 includes a destruction mechanism 24 and a transfer wheel 22. In an alternative embodiment, a pick-and-place device and accumulator device can be used in lieu of the transfer wheel 22.

The transfer wheel 22 accepts the carriers 12 as they arrive from the pipes 14 and 16 of the network 10. The transfer wheel 22 serves as a queue and houses the carriers 12 until they are ready for sterilization and destruction. The transfer wheel 22 can be connected to the destruction mechanism 24. In an alternative embodiment, the transfer wheel is independently supported by drive 17 and and operates in conjunction with the destruction mechanism 24.

Figure 3A:
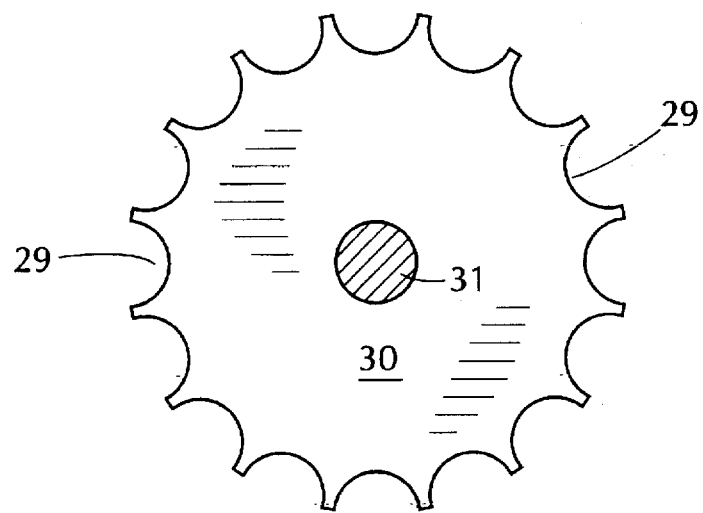
FIGS. 3A-3B illustrate a top view of a transfer wheel used with the syringe destruction apparatus shown in FIG. 2.
Figure 3B:
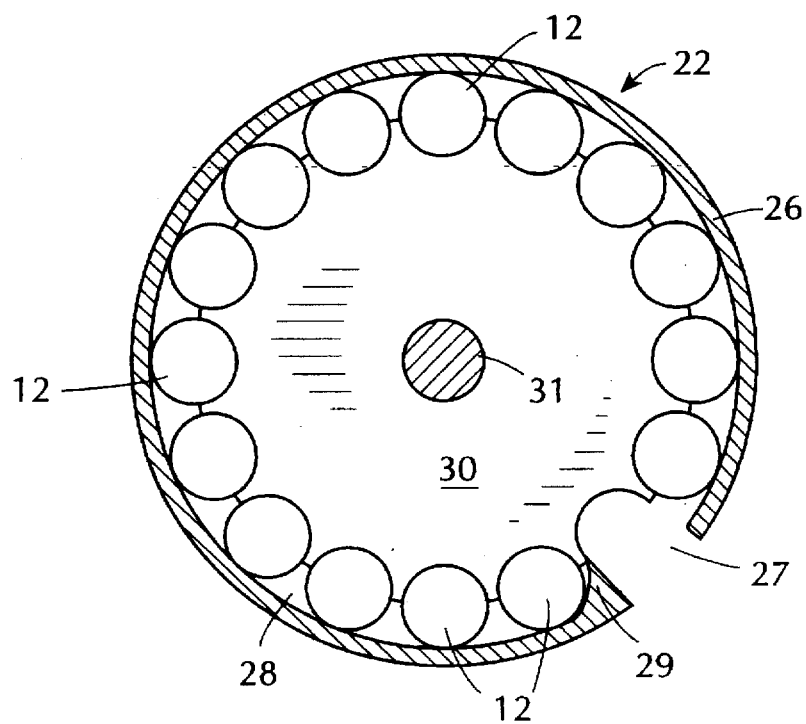

The transfer wheel 22, as shown in FIGS. 2 and 3A-3B, is constructed to function as a multi-station index wheel or accumulator that accepts the carriers 12 as they arrive from the pipes 14 and 16 and holds them for subsequent destruction by the destruction mechanism 24. The transfer wheel 22 consists of a cylindrical-shaped body 26, a circular base 28, two star-wheel guides 30, and a shaft 31. The shaft 31 is inserted through a hole in the bottom of the base 28 and is integrally connected to the star-wheel guides 30. When the shaft 31 is rotated, for example, by a pneumatic drive 17, the star-wheel guides 30 rotate in a clockwise direction within the the circular body 26. In an alternative embodiment, a stepper motor or Geneva mechanism may be used instead of the pneumatic drive 17.

The star-wheel guides 30 each include a plurality of circumferentially disposed pockets in the form of semicircular arcs 29 along their outer edge to receive carriers 12 received from the pipes 14 and 16 of the network 10. The base 28 and cylindrical body 26 each define a slot 27 into which a carrier 12 is moved when the shaft 31 is rotated. When a carrier 12 is placed into the slot 27, as will be described below, the carrier 12 will be ready for sterilization and destruction by the destruction mechanism 24. The cylindrical body 26 includes a stop 29 for preventing the next available carrier 12 from moving past slot 27 when the shaft 31 is rotated.

Figure 4:
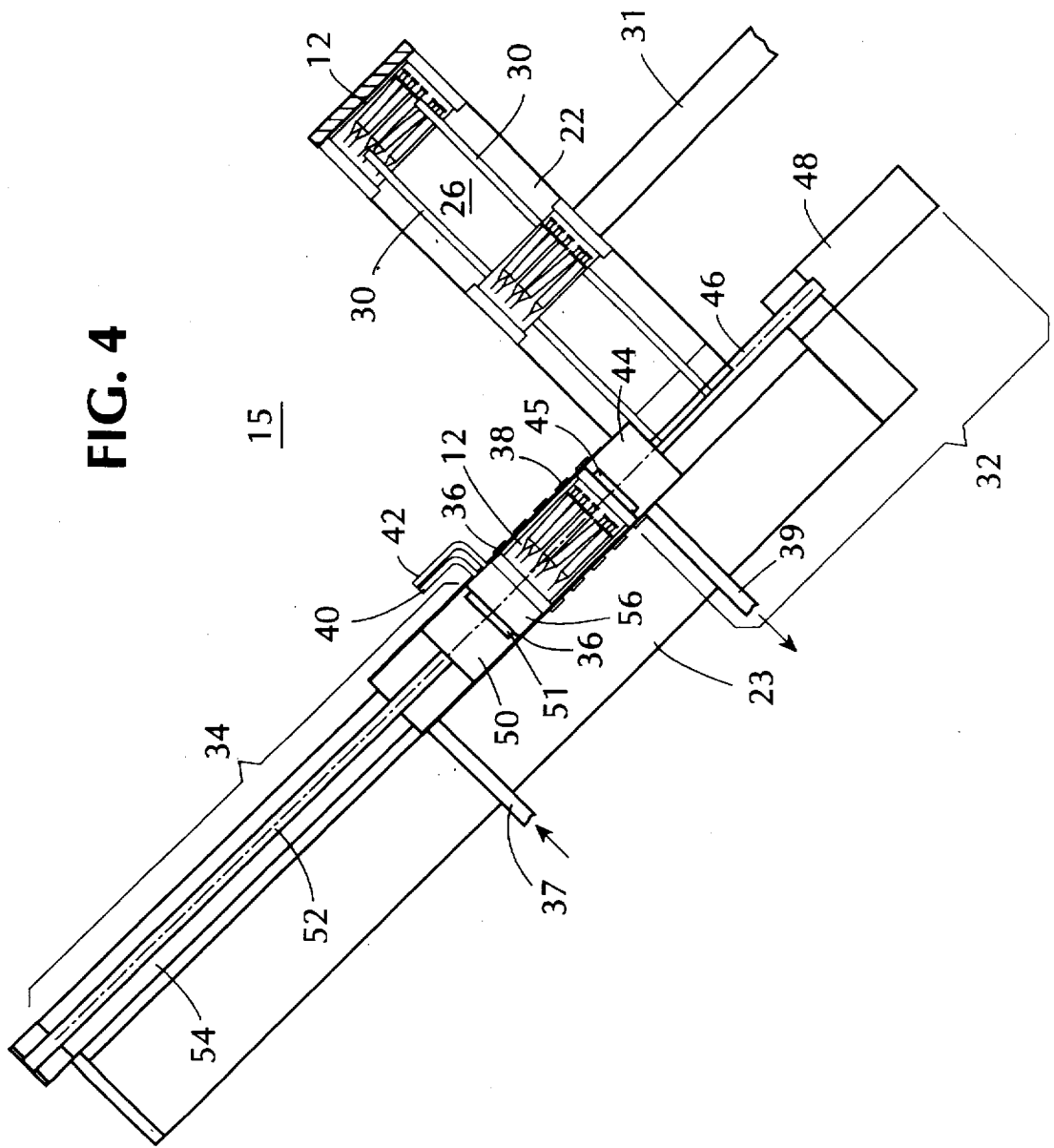
FIG. 4 illustrates the syringe destruction apparatus shown in FIG. 2 where a carrier has been placed in a compression chamber in accordance with the present invention.

Referring to FIG. 4, the destruction mechanism 24 sequentially destroys the carriers 12 as each is received from the transfer wheel 22. The destruction mechanism 24 includes a rigid body 23, a first piston mechanism 32, a second piston mechanism 34, a compression chamber 36, an induction coil 38, a water port 40, and a vacuum port 42.

The rigid body 23 functions as a base for supporting the destruction mechanism 24. The rigid body 23 can support the destruction mechanism 24 at an angle, as is shown in FIG. 4, or in a vertical position. Also, in an alternative embodiment discussed above, the rigid body 23 can support the transfer wheel 22.

The first piston mechanism 32 is affixed to the rigid body 23 and positioned directly beneath the slot 27 of the transfer wheel 22 such that it is in direct alignment with the compression chamber 36. The first piston mechanism includes a piston 44 which is connected to a rod 46. The rod 46 is mounted within a pneumatic cylinder or power screw 48. The pneumatic cylinder 48, when activated, extends the rod 46 such that the piston 44 contacts the carrier 12 placed in slot 27 of the transfer wheel and inserts the carrier 12 within the compression chamber 36.

The second piston mechanism 34 is affixed to the rigid body 23 and is positioned directly above the compression chamber 36. The second piston mechanism 23 is also in direct alignment with the compression chamber 36. The second piston mechanism includes a piston 50, rod 52, and pneumatic cylinder or power screw 54 which are interconnected in manner to the first piston mechanism 32. The pneumatic cylinder 54, when activated, extends the rod 52 such that the piston 50 is inserted into the compression chamber 36 to contact the carrier 12.

In an alternative embodiment, pistons 44 and 50 can include heating discs 45 and 51 to expedite the heating of the compression chamber 36.

The compression chamber 36 is attached to the rigid body 23 at a location beneath the second piston mechanism and above the transfer wheel 22. The compression chamber 36 receives the carrier 12 which is to be destroyed. The compression chamber 36 is longer than the carrier 12. As a result, once the carrier 12 is placed into the compression chamber 36, a space 56 is defined.

Water port 40 and vacuum port 42 are connected to the compression chamber 36. As will be described in detail below, during the destruction process, air is withdrawn from the space 56 through vacuum port 42 and water is injected into the space 56 through water port 40. The piston 50 covers the ports 40 and 42 at times during the compaction process to prevent clogging from melted plastic.

The induction coil 38 is connected to an outer surface of the compression chamber 36. Heat is produced almost instantaneously when a current is passed through the induction coil 38 by a generator. When current is passed through the induction coil 38, the compression chamber 36 and the carrier 12 placed within the compression chamber 36 are rapidly heated. In an alternative embodiment, a band heater can be used in lieu of the induction coil 38.

A fan, which is not shown, can be provided to cool the compression chamber 36 after it has been heated. Also, referring to FIGS. 4 and 5, a side wall 33 of the compression chamber 36 is designed to include a spiraling hollow passage 35. The hollow passage 35 is internally threaded within the side wall 33 of the compression chamber 36. The hollow passage 35 is connected to ports 37 and 39 which are attached to the compression chamber 36. The hollow passage 35 processes water to further assist in cooling the compression chamber 36. The water is injected into the hollow passage 35 through port 37 and removed through port 39.

Various embodiments of the carrier 12 can be used with the destruction mechanism 24. The carrier 12 is of a special construction and collects between 50 and 100 syringes before being placed in one of the pipes of the network 10.

Figures 6A, 6B:
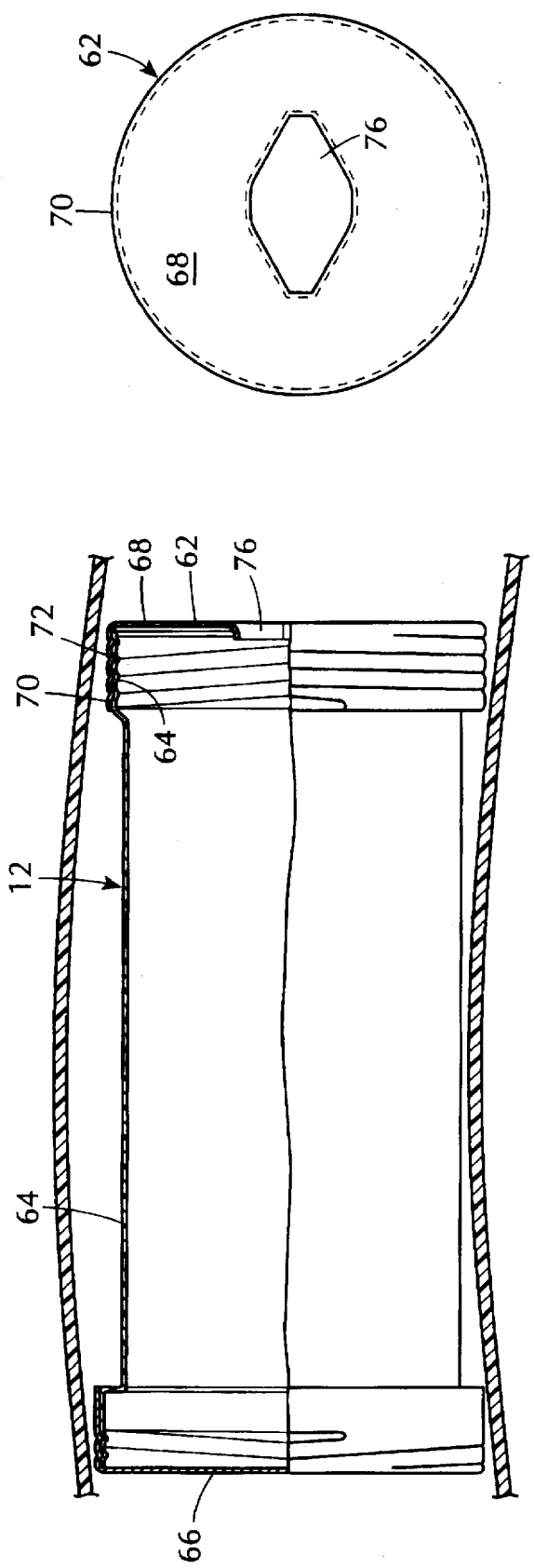
FIGS. 6A-6B illustrate a carrier used with a syringe destruction system in accordance with the present invention.

Referring to FIGS. 6A–6B, in one embodiment, the carrier 12 includes a first end 62, a plastic tube 64, and a second end 66. The first end 62 is made of metal and includes an flat surface 68 and a tubular side wall 70. The tubular side wall 70 includes threads 72 which mate with threads 74 placed on ends of the plastic tube 64. The flat surface 68 includes an opening 76 to receive used plastic syringes. The second end 66 is constructed the same as the first end 62, however, the second end 66 does not include an opening. The first and second ends 62 and 66 are threaded onto the plastic tube 64 to form the the carrier 12.

Figure 7B:
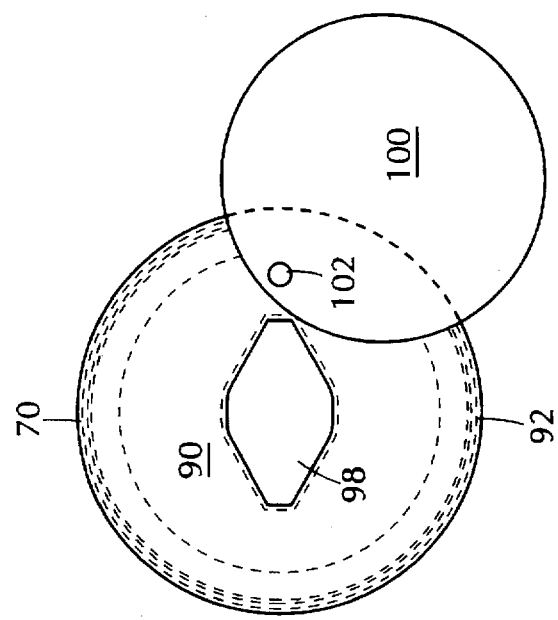
FIGS. 7A-7B illustrate an alternative embodiment of a carrier used with a syringe destruction system in accordance with the present invention.
Figure 7A:
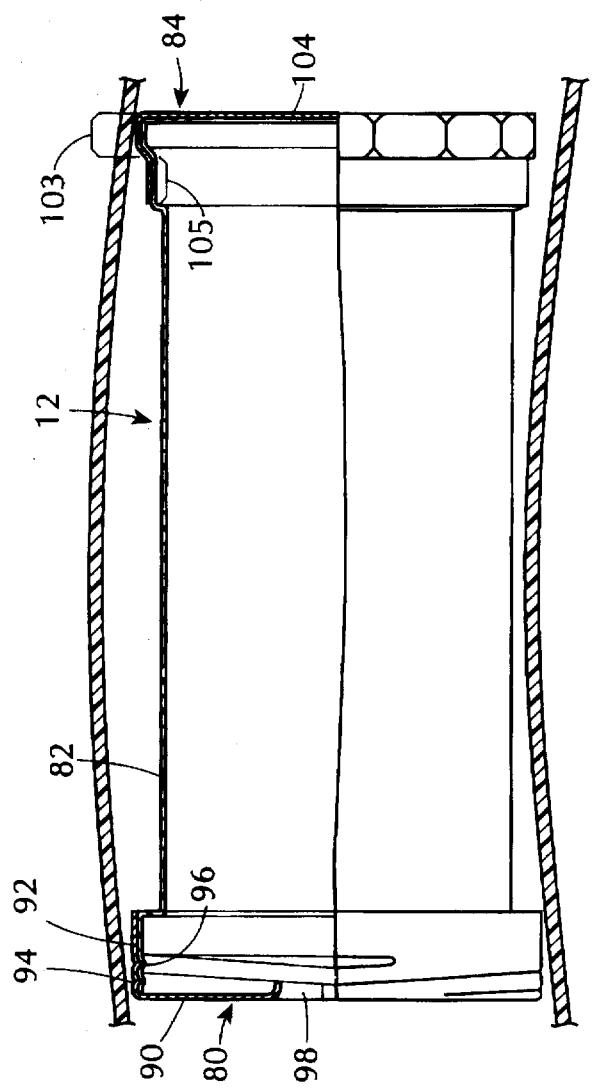

FIGS. 7A–7B shows a second embodiment of the carrier 12. This embodiment of the carrier 12 includes a first end 80, a plastic tube 82, and a second end 84. The first end 80 is made of metal and includes a flat surface 90 and tubular side wall 92. The tubular side wall 92 includes threads 94 which mate with threads 96 placed on the plastic tube 82. The flat surface 90 includes an opening 98 to receive used plastic syringes. A metal swing cover 100 is attached to the flat surface 90 by a screw, rivet or pivot shaft 102. After the used syringes are placed in the carrier 12, the swing cover 100 is rotated to cover the opening 98.

The second end 84 of the carrier 12 is also made of metal and includes a flat surface 104 and tubular side wall 106. The tubular side wall 106 includes a top portion 103 and a bottom portion 105, where the top portion 103 maintains a diameter which is larger than a diameter of the bottom portion 105. The second end 84 does not include an opening nor does it include threads.

In this embodiment, when the carrier 12 is constructed, the plastic tube 82 is first blow molded into the second end 84. After this is completed, the first end 80 is threaded onto the plastic tube 82.

In an alternative embodiment of the carrier 12, first and second metal ends are provided with tubular side walls which are press fit over open ends of a plastic tube. After the press fitting occurs, the first and second ends are ultrasonically welded to the plastic tube. In still another embodiment of the carrier 12, the plastic tube can include a slot to allow placement of syringes in the carrier 12 horizontally. This design will allow a larger number of syringes to be placed within the carrier 12.

FIG. 8 shows a side view of the carrier 12 in FIGS. 7A–7B after the carrier 12 has been compacted by the apparatus 15 described above. As can be seen from FIG. 8, the diameter of the tubular side wall 92 is designed to be larger than the diameter of the bottom portion 105 of the tubular side wall 106. As a result, once the carrier 12 is compacted, a metal container is formed to surround the syringes. This prevents any needles from protruding from an outer surface of the compacted carrier 12.

The metal ends of the various embodiments of the carriers 12 described above provide an additional advantage as well. In particular, the metal ends prevent needles of used syringes from penetrating the carrier 12 during the collection process. As a result, medical workers are further protected from being inadvertently stuck by a needle when loading a carrier 12 for destruction.

An operation of the invention will now be described with reference to the drawings. Referring to FIGS. 2 and 3A–3B, when the first piston mechanism 32 is retracted, rod 31 is rotated by motor 17 and the first available carrier 12 on the transfer wheel 22 is positioned into slot 27 of the transfer wheel 22 and above the first piston mechanism 32. The presence of the carrier 12 is detected by a sensor which is not shown.

When this occurs, as shown in FIG. 4, the first piston mechanism 32 is activated and the pneumatic cylinder 48 extends rod 46 and piston 44. The piston 44 contacts the carrier 12 and transfers it into the compression chamber 36.

At this point in the process, a current is passed through the induction coil 38 and the compression chamber 36 is heated to temperature at which the syringes can be sterilized. The metal ends of the carrier 12 and the metal needles of the syringes are exited by a flux generated from the induction coil 38 and help expedite the melting of the carrier 12 and its contents.

Once the compression chamber 36 reaches the desired temperature, a vacuum is applied to port 42 to evacuate any air residing in space 56 of the compression chamber 36. When the air is fully removed, water is injected into space 56 of the compression chamber 36 through port 40. Due to a lack of air pressure within the space 56, the injected water turns to steam. The steam resides within the compression chamber 36 for a time sufficient to soften the plastic syringes and sterilize the needles. Once this occurs, the steam is evacuated from the compression chamber 36 by a vacuum which is again applied to port 42.

Once the steam is evacuated, as shown in FIG. 9, the second piston mechanism 34 is activated and the pneumatic cylinder 54 extends rod 52 and piston 50. As a result, the piston 50 enters the compression chamber 36 and contacts the carrier 12 and compacts its mass against piston 44. When the piston 50 passes a certain position within the compression chamber 36, a sensor indicates its position and the current being supplied to heat the induction coil 38 is eliminated.

A fan, which is not shown, then begins cooling the compression chamber 36. Also, a cooling fluid, such as oil or water, is pumped through port 37 which is connected to the hollow passage 35 residing within the side wall 33 of the compression chamber 36 and removed from port 39. The cooling fluid can be any type of fluid with a boiling point higher than the temperature of the compression chamber 36 to allow a rapid cooling. The cooling fluid is continually pumped through ports 37 and 39 until the temperature of the compression chamber 36 reaches a temperature at which it plastic contents can be solidified. In an alternative embodiment, a heat exchanger can be utilized to expedite cooling and provide a shorter overall cycle time.

Figure 10:
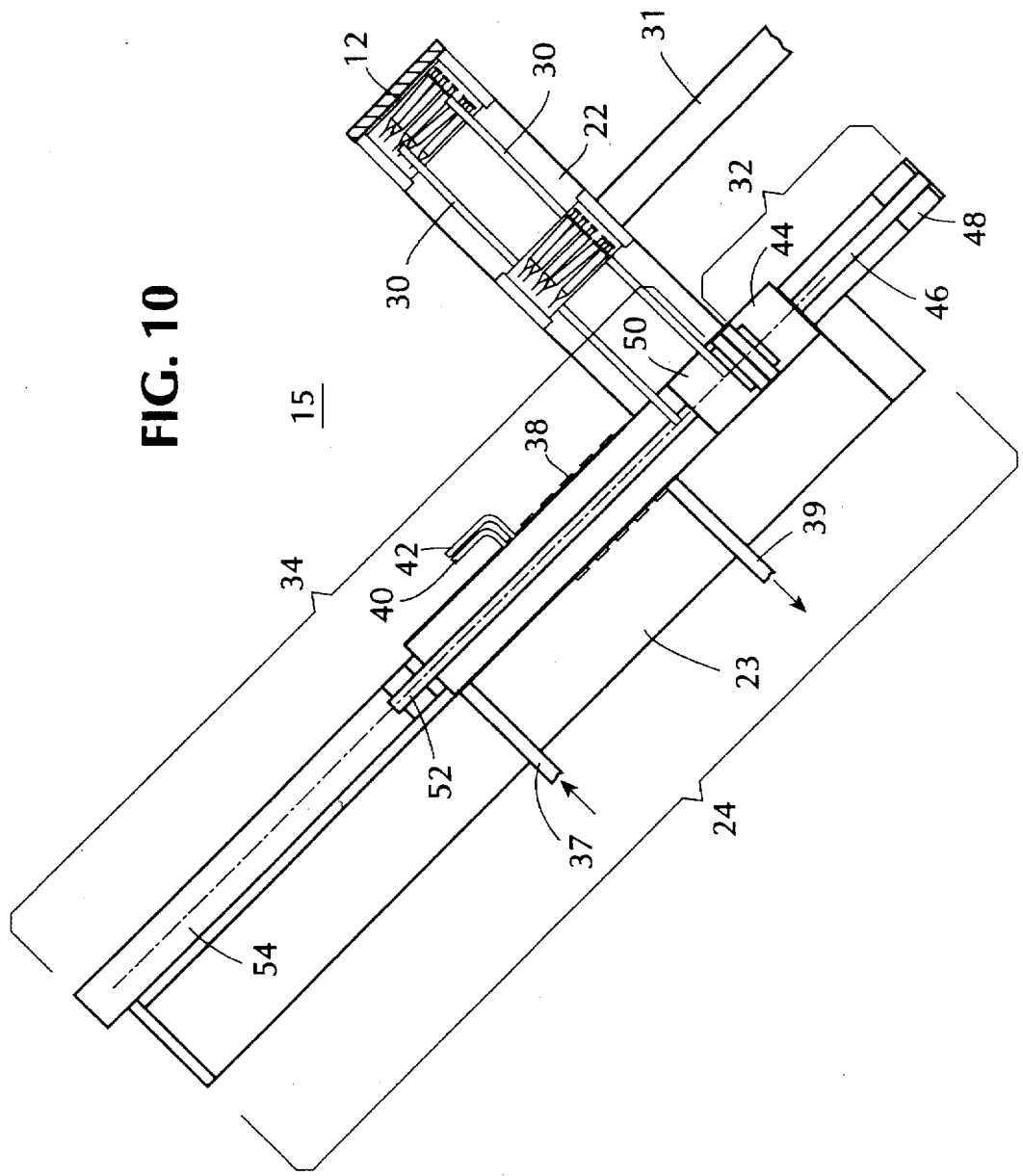

Referring to FIG. 10, when the temperature of the compression chamber 36 is cooled to the appropriate temperature, the piston 44 is retracted to its original position and the piston 50 is extended to its outer most position. When this occurs, the sterilized and compacted carrier 12 is placed in the opening above the piston 44 and falls into a refuse container which is not shown. The piston 50 is then retracted and the next available carrier 12 residing on transfer wheel 22 is placed above the piston 44 and another cycle is automatically performed.

It is of course to be understood that various changes may be made to embodiments of the automated syringe destruction system described above without departing from the scope of the invention. For example, the apparatus 15 for destroying and sterilizing carriers 12 can operate effectively without the use of a network 10. In particular, if carriers 12 are manually placed in the transfer wheel 22, the apparatus 15 will continue to cycle as described above until all stations on the transfer wheel 22 are displaced of carriers 12.

I claim:

1. An automated syringe destruction system comprising:

a carrier including plastic syringes requiring destruction and sterilization;

a network for receiving a plurality of said carriers from multiple locations and transporting said carriers to a centralized location; and means for destroying and sterilizing said carriers received from said network at said centralized location.

2. An automated syringe destruction system as defined in claim 1, wherein said means for destroying and sterilizing said carriers further comprises:

a transfer wheel for storing carriers received from said network; and, destruction means for compacting said carriers contained on said transfer wheel.

3. An automated syringe destruction system as defined in claim 2, wherein said destruction means further includes:

a rigid body;

a compression chamber which is attached to said rigid body above said transfer wheel, said compression chamber including first and second ends, a water port and a vacuum port;

first piston means for contacting one of said carriers stored on said transfer wheel and placing said carrier into said first end of said compression chamber, said first piston means being attached to said rigid body beneath said transfer wheel and in direct alignment with said compression chamber;

an induction coil surrounding said compression chamber for supplying heat to said compression chamber, said induction coil being connected to an outer surface of said compression chamber; and second piston means for entering said second end of said compression chamber to contact and compress said carrier against said first piston means, said second piston means being attached to said rigid body above said compression chamber and in direct alignment with said pressure chamber, wherein said water port supplies water to said compression chamber and said vacuum port applies a negative air pressure to said compression chamber.

4. An automated syringe destruction system as defined in claim 3, wherein said compression chamber includes a side wall which defines a hollow passage for processing water to cool said compression chamber.

5. An automated syringe destruction system as defined in claim 3, wherein said transfer wheel includes:

a circular base defining a slot and a hole;

a cylindrical-shaped body defining a slot which is attached to said circular base;

a shaft which is rotatably inserted into said hole; and at least one circular guide with semicircular arcs recessed along its outer edge for securing said carriers, said circular guide being rotatably fit within said cylindrical-shaped body and integrally connected to said shaft.

6. An automated syringe destruction system as defined in claim 3, wherein said carrier comprises:

a plastic tube including a first end and a second end;

a first cover including a first metal surface defining an opening and a first metal tubular side wall which is connected to said first metal surface;

a second cover including a second metal flat surface and a second metal tubular side wall which is connected to said second metal flat surface;

wherein, said first metal cover is connected to said first end of said plastic tube and said second metal cover is connected to said second end of said plastic tube.

7. An automated syringe destruction system as defined in claim 6, wherein said carrier further includes:

a pivot shaft which is attached to said first metal surface; and a swing cover which is is rotatably attached to said first metal surface by said pivot shaft to cover said opening.

8. An automated syringe destruction system as defined in claim 6, wherein a diameter of said first metal tubular side wall is larger than a diameter of said second tubular side wall.

9. A method for automatically destroying and sterilizing plastic syringes stored in a carrier, said method comprising the steps of:

(i) placing a plurality of carriers storing plastic syringes on a transfer wheel;

(ii) transferring one of said plurality of carriers placed on said transfer wheel into a first end of a compression chamber with a first piston means;

(iii) heating said compression chamber to a predetermined temperature;

(iv) applying a vacuum pressure to said compression chamber;

(v) injecting water into said compression chamber;

(vi) removing water from said compression chamber;

(vii) inserting a second piston means into a second end of said compression chamber to contact said carrier and compact said carrier against said first piston means; and, (viii) removing said compacted carrier from said compression chamber.

10. An automated syringe destruction system comprising:

a carrier including plastic syringes requiring destruction and sterilization;

a transfer wheel for storing carriers, and destruction means for compacting said carriers contained on said transfer wheel.

11. An automated syringe destruction system as defined in claim 10, wherein said destruction means further includes:

a rigid body;

a compression chamber which is attached to said rigid body above said transfer wheel, said compression chamber including first and second ends, a water port and a vacuum port;

first piston means for contacting one of said carriers stored on said transfer wheel and placing said carrier into said first end of said compression chamber, said first piston means being attached to said rigid body beneath said transfer wheel and in direct alignment with said compression chamber;

an induction coil surrounding said compression chamber for supplying heat to said compression chamber, said induction coil being connected to an outer surface of said compression chamber; and second piston means for entering said second end of said compression chamber to contact and compress said carrier against said first piston means, said second piston means being attached to said rigid body above said compression chamber and in direct alignment with said pressure chamber, wherein said water port supplies water to said compression chamber and said vacuum port applies a negative air pressure to said compression chamber.

* * * * *